(12) United States Patent
Chauhan et al.

(10) Patent No.: US 7,812,076 B2
(45) Date of Patent: Oct. 12, 2010

(54) ANTHRAPYRIDONE COMPOUNDS

(75) Inventors: Yogendrasinh Bharatsinh Chauhan, Valsad (IN); Kunal Hemant Mahajan, Thane (IN); Meerakani Mohamed Ali Sait, Tirunelveli (IN)

(73) Assignee: SABIC Innovative Plastics IP B.V., Bergen op Zoom (NL)

( * ) Notice: Subject to any disclaimer, the term of this patent is extended or adjusted under 35 U.S.C. 154(b) by 977 days.

(21) Appl. No.: 11/465,236

(22) Filed: Aug. 17, 2006

(65) Prior Publication Data

US 2008/0045634 A1 Feb. 21, 2008

(51) Int. Cl.
C08K 5/3415 (2006.01)
C08K 5/3432 (2006.01)
C08K 5/3437 (2006.01)
C07D 221/18 (2006.01)

(52) U.S. Cl. .......................... 524/89; 546/76
(58) Field of Classification Search ................... 546/76; 524/89
See application file for complete search history.

(56) References Cited

U.S. PATENT DOCUMENTS

| | | | |
|---|---|---|---|
| 4,386,206 A | 5/1983 | Wingard, Jr. et al. | |
| 4,902,798 A * | 2/1990 | Nakamatsu et al. | 546/76 |
| 5,183,892 A | 2/1993 | Nakamatsu et al. | |
| 5,367,075 A | 11/1994 | Nakamatsu et al. | |
| 6,245,118 B1 | 6/2001 | Shakhnovich | |
| 6,833,455 B2 | 12/2004 | Thiebes et al. | |
| 6,995,266 B2 | 2/2006 | Shankarling et al. | |
| 2006/0106140 A1* | 5/2006 | Shankarling et al. | 524/90 |

OTHER PUBLICATIONS

ASTM D4459-06 Standard Practice for Xenon-Arc Exposure of Plastics Intended for Indoor Applications, pp. 1-4.

* cited by examiner

Primary Examiner—Kriellion A Sanders

(57) ABSTRACT

A compound of Formula (I):

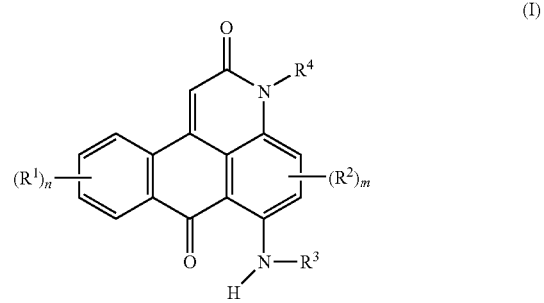

(I)

wherein $R^3$ is an aromatic functionality selected from the group consisting of Formula II and Formula III:

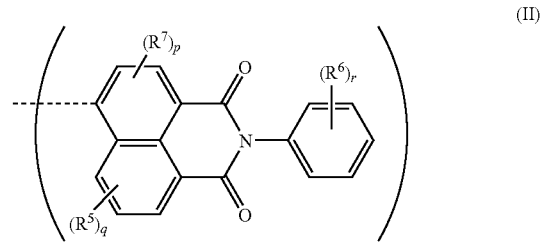

(II)

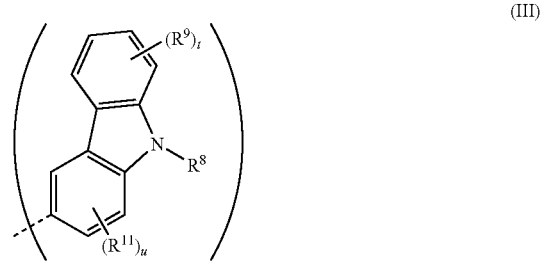

(III)

and wherein $R^1$, $R^2$, $R^5$, $R^6$, $R^7$, $R^9$, and $R^{10}$ are independently selected from the group consisting of an aliphatic functionality having 1 to 6 carbon atoms, an aromatic functionality having 3 to 20 carbon atoms, a cycloaliphatic functionality having 3 to 20 carbon atoms, a hydroxy group, a halogen group, and a cyano group; $R^4$ is an aliphatic functionality having 1 to 6 carbon atoms; $R^8$ is an aliphatic functionality having 1 to 6 carbon atoms; "n" has a value of 0 to 4; "m" has a value of 0 to 2; "p" has a value of 0 to 2; "u" has a value of 0 to 2; "q" has a value of 0 to 3; "t" has a value of 0 to 4; and "r" has a value of 0 to 5.

19 Claims, No Drawings

ANTHRAPYRIDONE COMPOUNDS

BACKGROUND

The present disclosure generally relates to anthrapyridone compounds. These anthrapyridone compounds are useful as thermally stable colorants in polymer compositions.

Colored polymer compositions are generally prepared by incorporating a colorant material in the polymer composition using processing techniques, such as extrusion or molding. The method of incorporating the colorant material depends upon, among other conditions, the nature of the polymer. For polymers that require high processing temperatures, for example greater than or equal to about 350° C., the colorant material should be thermally stable during the processing step. Examples of polymers that require such high processing temperatures include high heat polymers that have a glass transition temperature greater than that of bisphenol A homopolycarbonate. For example, polyetherimides such as ULTEM™ polyetherimide are examples of high heat polymers. Further, the colored polymer compositions so produced sometimes exhibit a color shift or a color that is different from the observed color of the colorant before it is included in the polymer compositions. The color shift is believed to occur due to the thermal instability of the colorant material. Additionally, the colorant materials in the colored polymer compositions can undergo degradation due to natural weathering, caused in part by sunlight, humidity, temperature, and the like.

Therefore there is a need for colorants that are resistant to thermal degradation, have good weatherability, and show little or no color shift when processed with polymers at elevated temperatures.

BRIEF SUMMARY

Disclosed herein is an anthrapyridone compound of Formula (I):

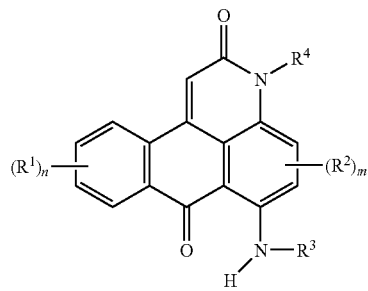

(I)

wherein $R^1$ and $R^2$ are independently selected from the group consisting of an aliphatic functionality having 1 to 6 carbon atoms, an aromatic functionality having 3 to 20 carbon atoms, a cycloaliphatic functionality having 3 to 20 carbon atoms, a hydroxy group, a halogen group, and a cyano group; $R^4$ is an aliphatic functionality having 1 to 6 carbon atoms; "n" has a value of 0 to 4; "m" has a value of 0 to 2; and $R^3$ is an aromatic functionality selected from the group consisting of Formula II and Formula III:

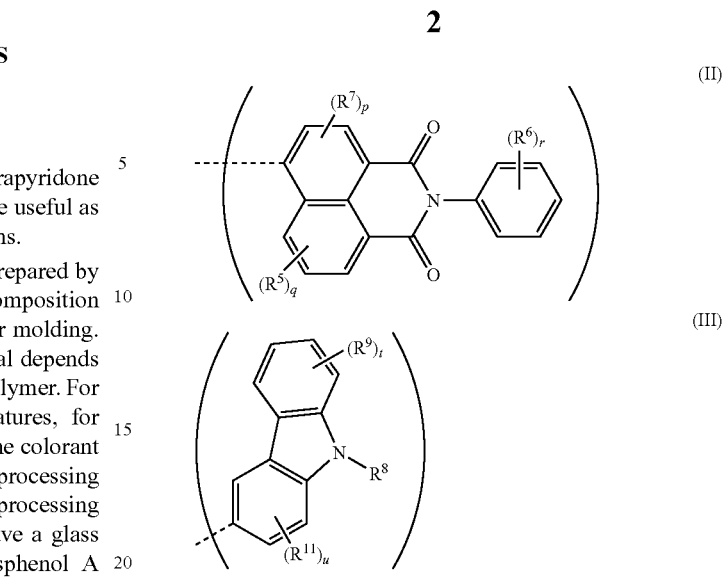

wherein $R^5$, $R^6$, $R^7$, $R^9$ and $R^{10}$ are independently selected from the group consisting of an aliphatic functionality having 1 to 6 carbon atoms, an aromatic functionality having 3 to 20 carbon atoms, a cycloaliphatic functionality having 3 to 20 carbon atoms, a hydroxy group, a halogen group, and a cyano group; $R^8$ is an aliphatic functionality having 1 to 6 carbon atoms; "p" has a value of 0 to 2; "q" and "u" each have a value of 0 to 3; "t" has a value of 0 to 4; and "r" has a value of 0 to 5.

In another embodiment, an anthrapyridone compound having a Formula (VI):

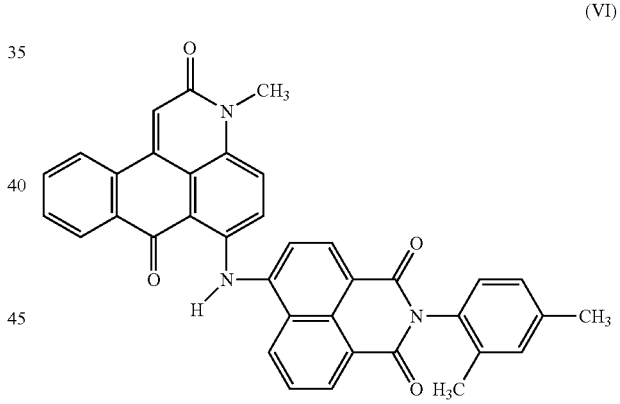

is disclosed.

In still another embodiment, an anthrapyridone compound having a Formula (VII):

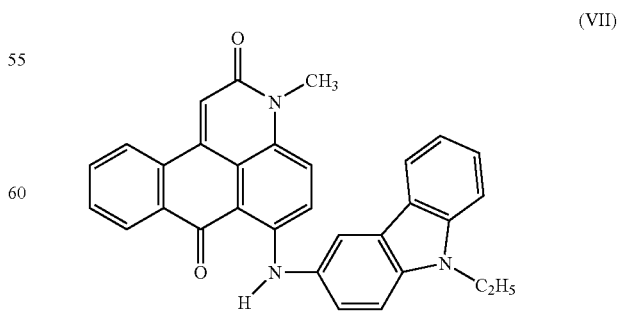

is disclosed.

In still another embodiment, an article comprising the anthrapyridone compound of Formula (I) is provided. In one embodiment, the article further comprises a thermoplastic resin, such as polycarbonate.

The disclosure may be understood more readily by reference to the following detailed description and the examples included therein.

DETAILED DESCRIPTION

Disclosed herein are anthrapyridone compounds represented by the general Formula (I):

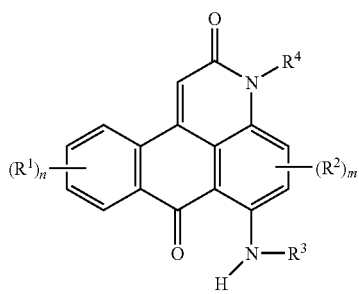

(I)

wherein $R^1$ and $R^2$ are independently selected from the group consisting of an aliphatic functionality having 1 to 6 carbon atoms, an aromatic functionality having 3 to 20 carbon atoms, a cycloaliphatic functionality having 3 to 20 carbon atoms, a hydroxy group, a halogen group, and a cyano group; $R^4$ is an aliphatic functionality having 1 to 6 carbon atoms; "n" has a value of 0 to 4; "m" has a value of 0 to 2; and $R^3$ is an aromatic functionality selected from the group consisting of Formula II and Formula III:

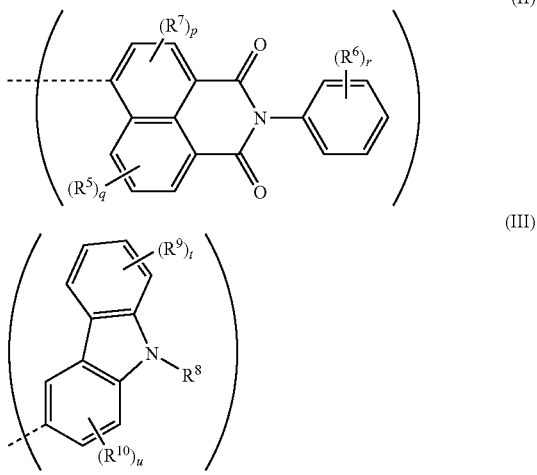

(II)

(III)

wherein $R^5$, $R^6$, $R^7$, $R^9$ and $R^{10}$ are independently selected from the group consisting of an aliphatic functionality having 1 to 6 carbon atoms, an aromatic functionality having 3 to 20 carbon atoms, a cycloaliphatic functionality having 3 to 20 carbon atoms, a hydroxy group, a halogen group, and a cyano group; $R^8$ is an aliphatic functionality having 1 to 6 carbon atoms; "p" has a value of 0 to 2; "q" and "u" each have a value of 0 to 3; "t" has a value of 0 to 4; and "r" has a value of 0 to 5. These anthrapyridone compounds are useful as thermally stable colorants in polymer compositions.

The singular forms "a", "an" and "the" include plural referents unless the context clearly dictates otherwise. All ranges disclosed herein are inclusive of the recited endpoint and independently combinable (for example ranges of "from about 2 grams to about 10 grams" is inclusive of the endpoints and all the intermediate values of the ranges of 2 grams to about 10 grams).

The modifier "about" used in connection with a quantity is inclusive of the stated value and has the meaning dictated by the context (for example, includes the degree of error associated with the measurement of the particular quantity).

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group. In chemical structures, a bond indicated by a dashed line ("-------") indicates an open position available for substitution.

As used herein, the term "cycloaliphatic functionality" designates cyclic aliphatic functionalities having a valence of at least one and comprising an array of atoms which is cyclic but which is not aromatic. A cycloaliphatic functionality may comprise one or more noncyclic components. For example, a cyclohexylmethyl group ($C_6H_{11}CH_2$) is a cycloaliphatic functionality, which comprises a cyclohexyl ring (the array of atoms which is cyclic but which is not aromatic) and a methylene group (the noncyclic component). The cycloaliphatic functionality may include heteroatoms such as nitrogen, sulfur, selenium, silicon and oxygen, or may be composed exclusively of carbon and hydrogen. For convenience, the term cycloaliphatic functionality is defined herein to encompass a wide range of functional groups such as alkyl groups, alkenyl groups, alkynyl groups, haloalkyl groups, conjugated dienyl groups, alcohol groups, ether groups, carboxylic acid groups, acyl groups (for example carboxylic acid derivatives such as esters and amides), amine groups and nitro groups. For example, the 4-methylcyclopent-1-yl group is a $C_6$ cycloaliphatic functionality comprising a methyl group, wherein the methyl group is a functional group which is an alkyl group. Similarly, the 2-nitrocyclobut-1-yl group is a $C_4$ cycloaliphatic functionality comprising a nitro group, wherein the nitro group is a functional group. A cycloaliphatic functionality may comprise one or more halogen atoms which may be the same or different. Exemplary cycloaliphatic functionalities comprise cyclopropyl, cyclobutyl, 1,1,4,4-tetramethylcyclobutyl, piperidinyl, 2,2,6, 6-tetramethylpiperydinyl, cyclohexyl and cyclopentyl.

As used herein, the term "aromatic functionality" refers to an array of atoms having a valence of at least one comprising at least one aromatic group. The array of atoms having a valence of at least one, comprising at least one aromatic group, may include heteroatoms such as nitrogen, sulfur, selenium, silicon and oxygen, or may be composed exclusively of carbon and hydrogen. As used herein, the term aromatic functionality includes but is not limited to, phenyl, pyridyl, furanyl, thienyl, naphthyl, phenylene, and biphenyl functionalities. The aromatic functionality may also include nonaromatic components. For example, a benzyl group is an aromatic functionality that comprises a phenyl ring (the aromatic group) and a methylene group (the nonaromatic component). Similarly a tetrahydronaphthyl functionality is an aromatic functionality comprising an aromatic group ($C_6H_3$) fused to a nonaromatic component ($CH_2$)$_4$. For convenience, the term aromatic functionality is defined herein to encompass a wide range of functional groups such as alkyl groups, haloalkyl groups, haloaromatic groups, alcohol groups, ether groups, carboxylic acid groups, acyl groups (for example carboxylic acid derivatives such as esters and amides), amine groups and nitro groups. For example, the 4-methylphenyl functionality is a $C_7$ aromatic functionality comprising a methyl group, wherein the methyl group is a functional group, which is an alkyl group. Similarly, the 2-nitrophenyl group is a $C_6$ aromatic functionality comprising a nitro group, wherein the nitro group is a functional group. Aromatic functionalities include halogenated aromatic functionalities. Exemplary aromatic functionalities include, but are not limited to, phenyl, 4-trifluoromethylphenyl, 4-chloromethylphen-1-yl, 3-trichloromethylphen-1-yl (3-$CCl_3$Ph-), 4-(3-bromoprop-1-yl)phen-1-yl (4-$BrCH_2CH_2CH_2$Ph-), 4-aminophen-1-yl (4-$H_2N$Ph-), 4-hydroxymethylphen-1-yl (4-$HOCH_2$Ph-), 4-methylthiophen-1-yl (4-$CH_3S$Ph-), 3-methoxyphen-1-yl and 2-nitromethylphen-1-yl (2-$NO_2CH_2$Ph), and naphthyl.

As used herein the term "aliphatic functionality" refers to a linear or branched array of atoms that is not cyclic and has a valence of at least one. Aliphatic functionalities are defined to comprise at least one carbon atom. The array of atoms may include heteroatoms such as nitrogen, sulfur, silicon, selenium and oxygen or may be composed exclusively of carbon and hydrogen. For convenience, the term aliphatic functionality is defined herein to encompass, as part of the "linear or branched array of atoms which is not cyclic" a wide range of functional groups such as alkyl groups, haloalkyl groups, alcohol groups, ether groups, carboxylic acid groups, acyl groups (for example carboxylic acid derivatives such as esters and amides), amine groups and nitro groups. For example, the 4-methylpent-1-yl is a $C_6$ aliphatic functionality comprising a methyl group, wherein the methyl group is a functional group, which is an alkyl group. Similarly, the 4-nitrobut-1-yl group is a $C_4$ aliphatic functionality comprising a nitro group, wherein the nitro group is a functional group. An aliphatic functionality may be a haloalkyl group which comprises one or more halogen atoms which may be the same or different. Exemplary aliphatic functionalities include, but are not limited to, methyl, ethyl, propyl, isopropyl, butyl, isobutyl, pentyl, isopentyl, trifluoromethyl, bromodifluoromethyl, chlorodifluoromethyl, chloromethyl, trichloromethyl, bromoethyl, 2-hexyl, hexamethylene, hydroxymethyl (i.e., $CH_2OH$), mercaptomethyl ($CH_2SH$), methylthio ($SCH_3$), methylthiomethyl ($CH_2SCH_3$), methoxy, methoxycarbonyl ($CH_3OCO$), nitromethyl ($CH_2NO_2$) and thiocarbonyl. The aliphatic, cycloaliphatic or the aromatic functionality may comprise a nitrogen-containing group that is generally non-reactive under the conditions used for preparing the anthrapyridone colorants disclosed herein. Further, the aliphatic, cycloaliphatic or the aromatic functionality may comprise a halogen functionality that is generally non-reactive under the conditions used for preparing the anthrapyridone colorants.

Various structural possibilities exist for the compounds of Formula (I). In one embodiment, $R^1$ and $R^2$ are independently selected from the group consisting of a halogen group, a cyano group, an aliphatic functionality having 1 to 4 carbon atoms, an aromatic functionality having 6 to 12 carbon atoms, and a cycloaliphatic functionality having 6 to 10 carbon atoms; $R^4$ is an aliphatic functionality having 1 to 4 carbon atoms; and $R^3$ is an aromatic functionality selected from the group consisting of Formula (II) and Formula (III):

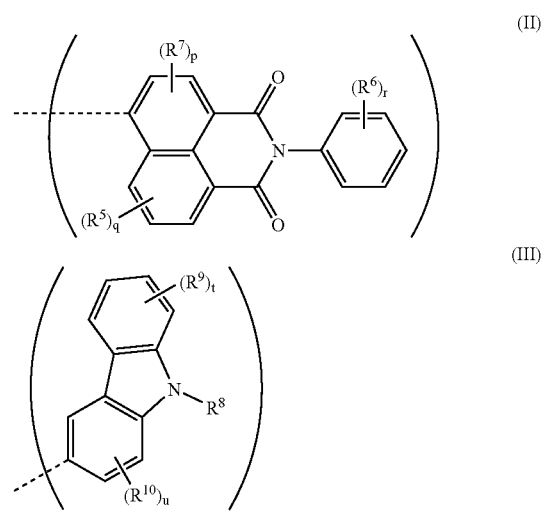

wherein $R^5$, $R^6$, $R^7$, $R^9$ and $R^{10}$ are independently selected from the group consisting of an aliphatic functionality having 1 to 4 carbon atoms, an aromatic functionality having 6 to 12 carbon atoms, a cycloaliphatic functionality having 6 to 10 carbon atoms, a hydroxy, a halogen group, and a cyano group; $R^8$ is an aliphatic functionality having 1 to 4 carbon atoms; and "n", "m", "p", "q", "u", "t", and "r" have values as described previously.

In another embodiment, $R^4$ is a methyl group; "n" and "m" each have a value of 0; and $R^3$ is an aromatic functionality having a Formula (IV):

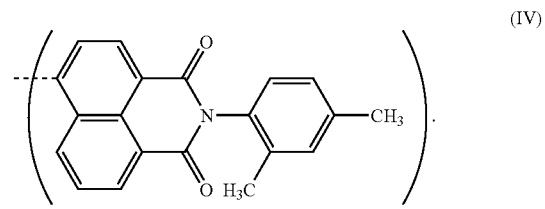

In yet another embodiment, $R^4$ is a methyl group; "n" and "m" each have a value of 0; and $R^3$ is an aromatic functionality having a Formula (V):

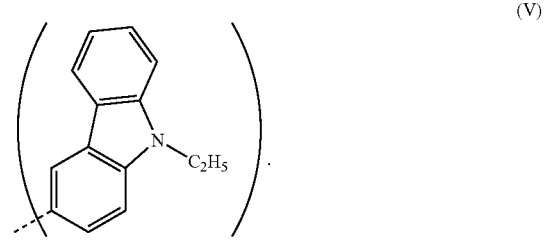

In a specific embodiment, a suitable anthrapyridone includes the compound 6-[2-(2,4-dimethylphenyl)-1,3-dioxo-2,3-dihydro-1H-benzo[de]isoquinolin-6-ylamino]-3-methyl-3H-naphtho[1,2,3-de]quinoline-2,7-dione, shown in Formula (VI):

(VI)

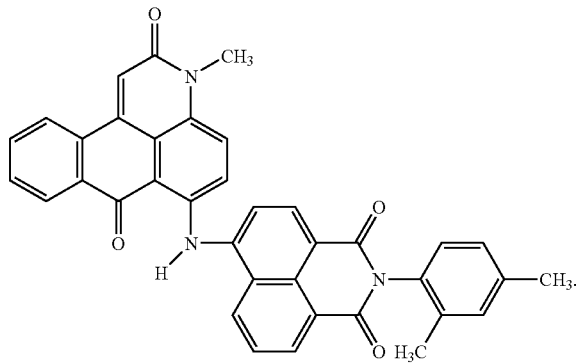

In another specific embodiment, an exemplary anthrapyridone includes 6-(9-ethyl-9H-carbozol-4-ylamino)-3-methyl-3H-naphtho[1,2,3-de]quinoline-2,7-dione, shown in Formula (VII):

(VII)

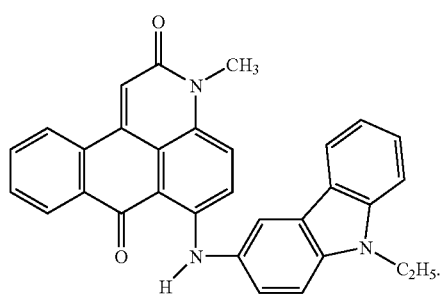

In accordance with one embodiment, the anthrapyridone compounds can be prepared by reacting a haloanthrapyridone compound with an amine compound in the presence of a catalyst composition and an acid-binding agent. Suitable haloanthrapyridone compounds are represented by the general Formula (VIII):

(VIII)

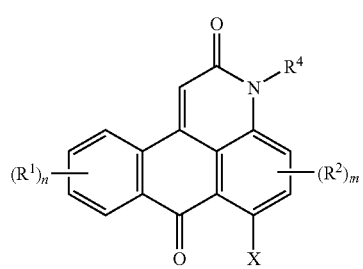

wherein $R^1$ and $R^2$ are independently selected from the group consisting of an aliphatic functionality having 1 to 6 carbon atoms, an aromatic functionality having 3 to 20 carbon atoms, a cycloaliphatic functionality having 3 to 20 carbon atoms, a hydroxy group, a halogen group, and a cyano group; $R^4$ is an aliphatic functionality having 1 to 6 carbon atoms; "n" has a value of 0 to 4; "m" has a value of 0 to 2; and X is a halogen atom selected from the group consisting of chlorine, bromine and iodine. The haloanthrapyridone compounds can be obtained by methods known in the art, such as for example, the method disclosed in U.S. Pat. No. 4,386,206, which is herein incorporated in its entirety. In one embodiment, the haloanthrapyridone compound comprises 6-bromo-3-methyl-3H-naphtho[1,2,3-de]quinoline-2,7-dione.

Suitable amine compounds are represented by the general Formula (IX):

$$R^3-NH_2 \qquad (IX)$$

wherein $R^3$ is an aromatic functionality selected from the group consisting of Formula II and Formula III:

(II)

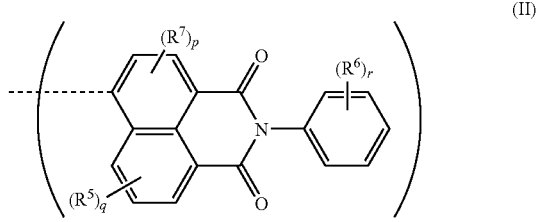

(III)

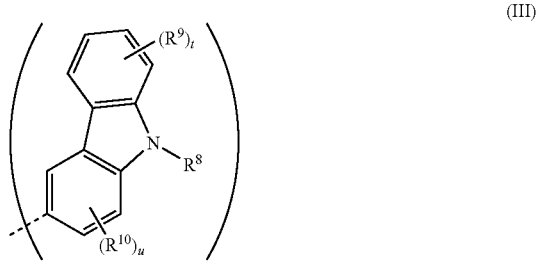

wherein $R^5$, $R^6$, $R^7$, $R^9$ and $R^{10}$ are independently selected from the group consisting of an aliphatic functionality having 1 to 6 carbon atoms, an aromatic functionality having 3 to 20 carbon atoms, a cycloaliphatic functionality having 3 to 20 carbon atoms, a hydroxy group, a halogen group, and a cyano group; $R^8$ is an aliphatic functionality having 1 to 6 carbon atoms; "p" has a value of 0 to 2; "q" and "u" each have a value of 0 to 3; "t" has a value of 0 to 4; and "r" has a value of 0 to 5. Suitable examples of amine compounds of Formula (IX) include 6-amino-2-(4-chloro-phenyl)-benzo[de]isoquinoline-1,3-dione, phosphoric acid 4-(6-amino-1,3-dioxo-1H, 3H-benzo[de]isoquinolin-2-yl)-phenyl dibutylester, 6-amino-2-phenyl-benzo[de]isoquinoline-1,3-dione, 6-amino-2-(2,4-dimethylphenyl)-benzo[de]isoquinoline-1,3-dione, and 3-amino-9-N-ethylcarbazole. In one embodiment, the amine compound is selected from 6-amino-2-(2,4-dimethylphenyl)-benzo[de]isoquinoline-1,3-dione and 3-amino-9-N-ethylcarbazole.

In accordance with another embodiment, the anthrapyridone compounds can be prepared by reacting an aminoanthrapyridone compound with an organohalogen compound in the presence of a catalyst composition and an acid-binding agent. Suitable aminoanthrapyridone compounds are represented by the general Formula (X):

(X)

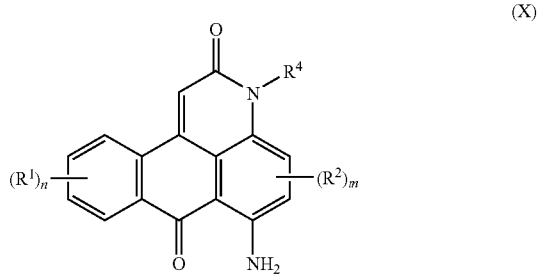

wherein $R^1$ and $R^2$ are independently selected from the group consisting of an aliphatic functionality having 1 to 6 carbon atoms, an aromatic functionality having 3 to 20 carbon atoms, a cycloaliphatic functionality having 3 to 20 carbon atoms, a hydroxy group, a halogen group, and a cyano group; $R^4$ is an aliphatic functionality having 1 to 6 carbon atoms; "n" has a value of 0 to 4; and "m" has a value of 0 to 2. In one embodiment, the aminoanthrapyridone compound comprises (6-amino-3-methyl-3H-naphtho[1,2,3-de]quinoline-2,7-dione).

Suitable organohalogen compounds are represented by the general Formula (XI):

wherein X is a halogen atom selected from the group consisting of chlorine, bromine and iodine; and $R^3$ is an aromatic functionality selected from the group consisting of Formula II and Formula III:

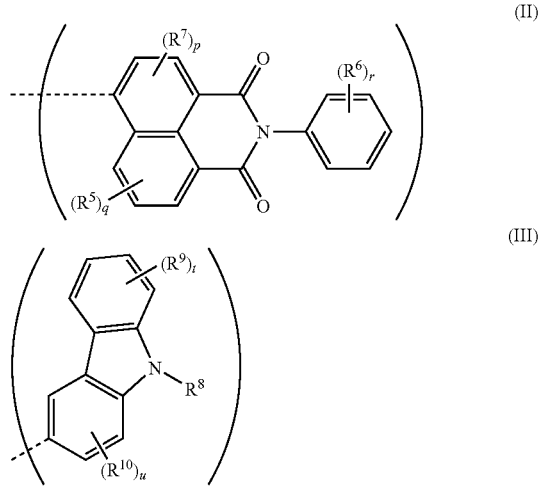

wherein $R^5$, $R^6$, $R^7$, $R^9$ and $R^{10}$ are independently selected from the group consisting of an aliphatic functionality having 1 to 6 carbon atoms, an aromatic functionality having 3 to 20 carbon atoms, a cycloaliphatic functionality having 3 to 20 carbon atoms, a hydroxy group, a halogen group, and a cyano group; $R^8$ is an aliphatic functionality having 1 to 6 carbon atoms; "p" has a value of 0 to 2; "q" and "u" each have a value of 0 to 3; "t" has a value of 0 to 4; and "r" has a value of 0 to 5. Suitable examples of organohalogen compounds of Formula (XI) include 9-acetyl-3-chloro-9H-carbazole, 3-bromo-9-ethyl-9H-carbazole, 9-ethyl-3-iodo-9H-carbazole, and 6-chloro-2-phenyl-1H-benzo[de]isoquinoline-1,3(2H)-dione.

The reaction of the amine compound with the haloanthrapyridone compound or the aminoanthrapyridone compound with the organohalogen compound is generally carried out in a non-aqueous solvent. Suitable examples of non-aqueous solvents include alkylbenzenes, such as for example toluene and xylene; organohalogen solvents, such as for example monochlorobenzene, 1,2-dichlorobenzene and 1,2,4-trichlorobenzene; amide solvents, such as for example N,N-dimethylformamide, N-methyl-3-pyrrolidinone, 1,3-dimethyl-2-imidazolidinone, and N,N-dimethylacetamide; dimethyl sulfoxide, sulfolane, nitrobenzene, and a combination of two or more of the foregoing solvents.

In one embodiment, the reaction of the haloanthrapyridone compound with the amine compound or the aminoanthrapyridone compound with the organohalogen compound is carried out at a temperature of about 100° C. to about 250° C. Within this range the reaction is carried out at a temperature greater than or equal to about 120° C., or more specifically greater than or equal to about 150° C. Also within this range the reaction is carried out a temperature less than or equal to about 240° C., or more specifically less than or equal to about 230° C. In one embodiment the time required for the reaction of the haloanthrapyridone compound with the amine compound or the aminoanthrapyridone compound with the organohalogen compound is about 8 hours to about 50 hours. Within this range the time required for the reaction is greater than or equal to about 10 hours, or more specifically greater than or equal to about 12 hours. Also within this range the time required for the reaction is less than or equal to about 48 hours, or more specifically less than or equal to about 24 hours.

For either method of preparing the anthrapyridone compounds, the catalyst composition comprises either copper or a copper salt. Copper salts are typically selected from the group consisting of copper (I) halide salts and copper (II) halide salts. Other copper salts such as organic copper salts, exemplified by copper (II) acetate can also be used. The amount of the catalyst composition employed comprises about 0.005 to about 0.2 moles per mole of the aminoanthrapyridone or the haloanthrapyridone compound used. Specific examples of the catalyst composition include cupric acetate, cupric iodide, cuprous chloride, cuprous bromide, cuprous iodide, cuprous sulfate, cuprous acetate, cuprous formate, and a combination of two or more of the foregoing copper salts.

Acid-binding agents are typically employed in either method of preparing the anthrapyridone compounds to trap the hydrogen halide generated in the reaction. Suitable acid-binding agents include but are not limited to alkali metal carbonates, alkaline earth metal carbonates, alkali metal bicarbonates, alkaline earth metal bicarbonates, alkali metal carboxylates, and alkaline earth metal carboxylates having the general formula $M(COOR^{11})_v$, wherein "M" is an alkali metal or an alkaline earth metal; $R^{11}$ is an aliphatic functionality having about 1 to about 6 carbons; and "v" has a value of 1 or 2. Specific examples of the acid-binding agents include potassium acetate, potassium carbonate, sodium carbonate, sodium acetate, potassium bicarbonate, sodium benzoate, and sodium bicarbonate.

The methods described hereinabove can be conducted either in a batch process or with suitable modifications in a semi-continuous process or a continuous process, as would be apparent to one skilled in the art.

The anthrapyridone compounds disclosed herein are useful as colorant materials, more specifically as thermally stable colorants for incorporation in polymer compositions. As such, the colorant materials are attractive materials for use with polymers having high glass transition temperatures and/or high processing temperatures. There are many polymers that require high processing temperatures, for example greater than or equal to about 350° C. The polymer processing equipment, such as molding machines and extruders, are typically operated at temperatures less than or equal to about 450° C., and more specifically at temperatures of about 250° C. to about 420° C. The anthrapyridone compounds disclosed herein are suitable for coloring these polymers as they typically have a decomposition onset temperature of greater than or equal to 350° C. Additionally, the anthrapyridone compounds can also be used in other applications, such as for example dyeing, as printing inks, and others.

The anthrapyridone compounds are valuable colorants for producing colored polymer compositions and colored molded polymer articles therefrom having superior properties, such as excellent heat resistance, superior light resistance, bleeding resistance, extraction resistance, and sublimation resistance. The anthrapyridones can be directly used in the solid state for example, in the powder form, or used as a solution in a suitable solvent during a molding or an extrusion step. In general, any non-aqueous solvent can be used.

Any thermoplastic polymer known in the art can be used for producing the colored molded articles. Further, the polymer compositions can comprise one or more thermoset polymers. Non-limiting examples of thermoplastic polymers include polystyrene, poly(methymethacrylate), poly(vinyl chloride), acrylonitrile-butadiene-styrene copolymer (ABS), acrylonitrile-styrene-acrylate copolymer (ASA), styrene-acrylonitrile copolymer (SAN), polycarbonate, poly(phenyleneoxide), polyolefins, such as polypropylene and polyethylene, poly(acrylonitrile), polyamide, polyacetal, polyesters such as poly(ethyleneterephthalate) and poly(butyleneterephthalate), polyetherimides, such as ULTEM™ polyetherimide, and any mixture of the foregoing thermoplastic polymers. Non-limiting examples of the thermoset polymers include phenolic resins, urea resins, melamine resins, unsaturated polyester resins, epoxy resins and poly(diallylphthalate) resin.

Colored polymer compositions are generally obtained by blending the anthrapyridone compound with polymers in a suitable manner, and subjecting the resulting blend to a molding step using techniques, such as injection molding, extrusion, and melt-spinning. For instance, pellets or powders of the polymer are mixed with a pulverized coloring agent in a suitable mixer and then the mixture is treated in a kneader, roller mill, Banbury™ mixer or an extruder, until the coloring agent is dissolved or dispersed in the polymer. The amount of anthrapyridone compound in the polymer is not critical, but generally it is sufficient to use about 0.01 weight percent to about 5 weight percent, based on the weight of the polymer. Within this range the amount of anthrapyridone compound is greater than or equal to about 0.02 weight percent, or more specifically greater than or equal to about 0.05 weight percent, based on the weight of the polymer. Also within this range the amount of anthrapyridone compound is less than or equal to about 2 weight percent, or more specifically less than or equal to about 1 weight percent, based on the weight of the polymer.

If desired, the resulting colored polymer composition can be further subjected to a molding step to make colored molded articles using techniques such as compression molding, injection molding, and blow molding. Alternatively, the anthrapyridone compound may be mixed with a monomer containing a polymerization catalyst, followed by polymerization to obtain a colored thermoplastic or thermoset polymer in situ. In one embodiment is provided an article comprising polycarbonate and the anthrapyridone compound of Formula (VI). In another embodiment is provided an article comprising polycarbonate and the anthrapyridone compound of Formula (VII).

The anthrapyridone compounds disclosed herein may also be used optionally with other colorants, such as for example pigments and dyes, as well as with filler materials and other additives known in the art. Additives may include stabilizers, mold release agents, processing aids, flame retardants, drip retardants, nucleating agents, UV blockers, dyes, pigments, particulate, conductive fillers, such as for example conductive carbon black and carbon nanotubes, reinforcing fillers, antioxidants, anti-static agents and blowing agents.

A further understanding of the techniques described above can be obtained by reference to certain specific examples that are provided herein for purposes of illustration only and are not intended to be limiting.

EXAMPLES 6-bromo-3-methyl-3H-naphtho[1,2,3-de]quinoline-2,7-dione (98 percent pure) used in the synthesis of the anthrapyridone compounds was procured from Jiangsu Aolunda High-Tech Industry Limited, China; 6-amino-2-(2,4-dimethylphenyl)-benzo[de]isoquinoline-1,3-dione (C.I. Solvent Yellow 44; 99 percent pure) was procured from Neelikon Food Dyes and Chemicals Limited, India; 3-amino-9-N-ethylcarbazole (80 percent pure) was procured from Aldrich Chemicals, U.S.A.; and 3-methyl-6-(p-tolylamino)-3H-naphtho[1,2,3-de]quinoline-2,7-dione (C.I. Solvent Red 52; 99 percent pure) was procured from Devarsons, India. Bisphenol A homopolycarbonate (having a molecular weight of about 40,000 daltons measured using polystyrene standards) was obtained from GE Plastics. All other reagents were procured from Aldrich Company, U.S.A. and Lancaster Chemical Company, U.K.

Proton NMR spectra for all the anthrapyridone compounds described herein were measured using a 300 megahertz Bruker™ NMR spectrometer using $CD_2Cl_2$ as the solvent. The sample for the analysis was prepared by dissolving about 7 to 10 milligrams (mg) of the anthrapyridone compound in 0.5 milliliters (ml) of $CD_2Cl_2$.

The anthrapyridone compound was further characterized by using a liquid chromatograph-mass spectrometer (LC-MS) system, comprising an Alliance Systems liquid chromatograph with the column output coupled with a Quattro Ultima Pt mass spectrometer. A sample solution was prepared by dissolving 10 to 15 mg of the product in 10 ml of dichloromethane. The sample solution was then diluted with 15 ml of acetonitrile. The mobile phase comprised a 70:30 volume/volume mixture of 0.05 percent formic acid in water and 0.05 percent formic acid in acetonitrile. This diluted sample was injected into an Xterra C18 column having a length of 50 millimeters (mm), a diameter of 4.6 mm, and a column packing having a pore size of 5 microns. A flow rate of 1.0 milliliters per minute (ml/minute) of the eluent and a column temperature of 30° C. was employed for separating the components. The product and other components were characterized by mass spectrometry. A plot of mass to charge ratio (m/z) versus the percentage molecular ion abundance led to the identification of the desired anthrapyridone compound as the molecular ion with the highest relative abundance.

UV-visible absorbance was measured using a double beam Perkin Elmer® Lambda 900 UV-VIS-NIR spectrophotometer. About 11.2 grams (g) of the anthrapyridone compound was dissolved in 100 ml of dichloromethane to obtain a stock solution. A 10 ml portion of the stock solution was further diluted to 100 ml using dichloromethane and utilized for the absorption measurements. The measurement was made in the absorption mode of the instrument over a wavelength range from 200 nanometers (nm) to 700 nm.

Thermogravimetric analysis (also referred to as "TGA") was carried out using a TGA 2950 instrument equipped with an auto sampler, and available from TA Instruments. TGA measures the amount of weight change in a material as a function of temperature in a controlled atmosphere. TGA can be carried out either using a programmed temperature setting whereby the sample is heated at a pre-determined rate, or the sample is subjected to a constant temperature (isothermal condition). In the present disclosure the sample was equilibrated to an initial temperature of 40° C. for a period of 2 to 3 minutes and then heated at the rate of 10° C. per minute up to a maximum temperature of 600° C. under air. The weight of the sample was monitored continuously throughout the heating process. Any weight loss is generally indicative of decomposition or degradation of the sample. This technique was used to measure the thermal stability for the anthrapyridone compounds disclosed herein. The thermal stability data in turn was used to identify anthrapyridone compounds that can be beneficially used as colorants in colored polymer compositions. In general the higher the decomposition temperature of an anthrapyridone compound, the more suitable it will be as a colorant for high temperature compositions and high temperature end uses. A weight loss temperature curve can be generated from the TGA experiment. The TGA results are expressed in terms of $T_d$ (also referred to as Decomposition Onset Temperature). For the purposes of this disclosure, $T_d$ represents the inflection point on the weight loss temperature curve. In other words, $T_d$ is the temperature corresponding to the point at which the tangent to the curve has the highest slope.

Infrared (IR) spectra were obtained by using a Perkin Elmer® Spectrum GX series instrument. About 40 mg of the anthrapyridone compound was directly placed on the diamond interface of the instrument and analyzed by measuring transmittance over a range from 500 reciprocal centimeters (denoted as $cm^{-1}$) to 4000 $cm^{-1}$.

Thin-layer chromatography (TLC) was performed using silica gel (60 mesh) F254 pre-coated plates, which were procured from E. Merck. The eluent system used was a 7:2:1 (volume by volume by volume) toluene, ethylacetate, and glacial acetic acid, respectively.

Example 1 describes the preparation of 6-[2-(2,4-dimethylphenyl)-1,3-dioxo-2,3-dihydro-1H-benzo[de]isoquinolin-6-ylamino]-3-methyl-3H-naphtho[1,2,3-de]quinoline-2,7-dione, shown as Formula (V).

To a three-necked round-bottomed flask equipped with a thermometer and a Dean-Stark apparatus was charged 6-amino-2-(2,4-dimethylphenyl)benzo[de]isoquinoline-1,3-dione (4.69 g), potassium acetate (1.443 g), potassium carbonate (2.032 g), cupric acetate (0.1262 g), cupric iodide (0.120 g), and ortho-dichlorobenzene (45 ml) to obtain a mixture. The mixture was heated to 120° C. in about 10 minutes. After being maintained at 120° C. for about 30 minutes, 6-bromo-3-methyl-3H-naphtho[1,2,3-de]quinoline-2,7-dione (5 g) and ortho-dichlorobenzene (45 ml) were added to the mixture. Then the temperature of the resulting reaction mixture was raised to 165° C. over a period of about 1.5 hours. After being maintained at this temperature for about 4 hours, formation of a red solid was observed. A portion of the reaction mixture was spotted on a TLC plate and viewed under ultraviolet radiation to monitor the disappearance of the starting materials 6-amino-2-(2,4-dimethyl)phenyl-benzo[de]isoquinoline-1,3-dione and 6-bromo-3-methyl-3H-naphtho[1,2,3-de]quinoline-2,7-dione. After being heated for 2 more hours at the same temperature, TLC analysis of the reaction mixture indicated the absence of both the starting materials. The reaction mixture was then cooled, poured into 175 ml of methanol, filtered, and the filter cake was washed with 2 to 3 100 ml portions of methanol to give the desired product in a yield of 7.2 g.

Proton NMR of the product showed peaks at δ 2.09 to 2.34 (3H, s, Ar—$CH_3$), 3.82 (3H, s, N—$CH_3$), 7.05 to 7.17 (3H, m, Ar—CH) and 7.6 to 8.6 (12H, m, Ar—CH). LC-MS gave a molecular ion peak (M+) having a mass of 576.32 amu (atomic mass units). UV-Visible spectrum of the product in dichloromethane as a solvent showed an absorbance maximum at 530 nm. The anthrapyridone compound showed a weight loss of 9.08 percent at a decomposition onset temperature of 410° C., as measured using the TGA technique described above.

Example 2 describes the preparation of 6-(9-ethyl-9H-carbozol-4-ylamino)-3-methyl-3H-naphtho[1,2,3-de]quinoline-2,7-dione compound, Formula (VII).

To a three-necked round-bottomed flask equipped with a thermometer and a Dean-Stark apparatus was charged 3-amino-9-N-ethylcarbazole (3.12 g), potassium acetate (1.442 g), potassium carbonate (2.031 g), cupric acetate (0.208 g), cupric iodide (0.191 g), and ortho-dichlorobenzene (45 ml) to obtain a mixture. The mixture was heated to 120° C. over a period of about 10 minutes, and maintained at this temperature for about 30 minutes. Then 6-bromo-3-methyl-3H-naphtho[1,2,3-de]quinoline-2,7-dione (5 g) and ortho-dichlorobenzene (45 ml) were added to the mixture. The temperature of the resulting reaction mixture was raised to 165° C. over a period of about 1.5 hours. After being maintained at this temperature for about 4 hours, formation of a purple red solid was observed. A portion of the reaction mixture was spotted on a TLC plate and viewed under ultraviolet radiation to monitor the disappearance of the starting materials 3-amino-9-N-ethylcarbazole and 6-bromo-3-methyl-3H-naphtho[1,2,3-de]quinoline-2,7-dione. After being heated for 2 more hours at the same temperature, TLC analysis of the reaction mixture indicated the absence of both the starting materials. The reaction mixture was then cooled to ambient temperature, poured into 175 ml of methanol, filtered, and the filter cake was washed with 2 to 3 portions of 100 ml of methanol to provide a crude product. The crude product was then dissolved in dichlormethane and purified by column chromatography using silica gel (60 mesh size) as the column packing and a 80:20 mixture (volume by volume) of ethyl acetate and acetone, respectively. The desired product was isolated in a pure form in a yield of 3.7 g.

Proton NMR of the product showed peaks at δ 1.44 (3H, t, $CH_2CH_3$), 3.80 (3H, s, N—$CH_3$), 4.34 (2H, q, $CH_2CH_3$), 7.37 to 8.60 (15H, m, Ar—CH) and 12.11 (1H, s, N—H). LC-MS gave a molecular ion peak (M+) having a mass of 470.43 amu. UV-Visible spectrum of the product in dichloromethane as a solvent showed absorbance maxima at 540 nm and 560 nm. The product showed a weight loss of 6.39 percent at a decomposition onset temperature of 360° C. when analyzed using thermogravimetric analysis.

The general procedure used for preparing extruded polymer samples incorporating the anthrapyridone compounds described above is as follows. A 1 kilogram sample of bisphenol A homopolycarbonate and 0.02 weight percent (based on the total sample weight) of each of the anthrapyridone compounds of Example 1 and Example 2 was taken in a polyethylene bag and shaken vigorously for about 3 to 5 minutes. The resultant mixture was then compounded using a Werner and Pfleiderer™ Twin Screw Extruder, Model ZSK-25 Mega Compounder under vacuum under the conditions specified in Table 1 to produce colored polymer pellets.

TABLE 1

| | |
|---|---|
| Feed zone temperature (° C.) | 128 |
| Zone 1 temperature (° C.) | 280 |
| Zone 2 temperature (° C.) | 285 |
| Zone 3 temperature (° C.) | 285 |

TABLE 1-continued

| | |
|---|---|
| Zone 4 temperature (° C.) | 290 |
| Throat/Die temperature (° C.) | 290 |
| Screw speed (Revolutions per minute) | 300 |
| Temperature of Melt (° C.) | 300 |
| Torque (Nm) | 58-62 |

The extruded pellets were dried in an oven maintained at 120° C. for about 4 hours. Then the dried pellets were subjected to molding using a LTM-Demag molding machine to provided step-chips. Step-chips can be defined as single molded chips having sections of 1, 2 and 3 millimeters (mm) thickness down the length of the chip. The step-chips are useful for weatherability studies. The conditions for preparing the step-chips are shown in Table 2, where [s] indicates time in seconds.

TABLE 2

Conditions for preparing the step-chips.

| | |
|---|---|
| Cycle Time [s] | 900.00 |
| Blocking Time [s] | 60.00 |
| Pause Time [s] | 0.00 |
| Delay Injection [s] | 1.00 |
| Injection Pressure [bar] | 95.00 |
| Injection Speed [mm/s] | 75.00 |
| Holding Pressure Release [s] | 1.00 |
| Holding Time Step 1 [s] | 13.00 |
| Holding Pressure Step 1 [bar] | 80.00 |
| Cooling Time [s] | 15.00 |

The molded chips incorporating the anthrapyridone compound were subjected to a weatherability test by using an Atlas Ci4000 weatherometer following the conditions laid out in Tables 3 to 6 of ASTM D4459 test method for in-door applications, Table 7 of ISO 4892-2A test method for external applications, and Table 8 of SAE J1960 test method (Society of Automotive Engineers Standards). A D65 illuminator was used since it most closely simulates natural sunlight. After being exposed for about 300 hours, the color of the sample was analyzed in the transmittance mode using a Macbeth Color Eye 7000A instrument equipped with an integrating sphere. The settings used included an observer of 10 degrees, a color space from about 360 nm to about 760 nm, and the specular component. Sample measurements were made at exposure times of zero (that is, before being placed in the Weatherometer), 100, 200, and 300 hours of exposure. The various parameters shown in Table 3 are: $L^*$: Lightness; $a^*$: redness-greenness, $b^*$: yellowness-blueness; $C^*$: chroma; and $H^*$: hue. The various parameters shown in Table 4 are: $\Delta L^*$: the difference in lightness before and after exposure in weatherometer; $\Delta a^*$: the difference in redness-greenness before and after exposure in weatherometer; $\Delta b^*$: the difference in yellowness-blueness before and after exposure in weatherometer; $\Delta C^*$: the difference in chroma before and after exposure in weatherometer; $\Delta H^*$: the difference in hue before and after exposure in weatherometer; and $\Delta E^*$: the total color difference between the values obtained before and after exposure in the weatherometer. $\Delta E^*$ is derived from the $\Delta a^*$, $\Delta b^*$, and $\Delta L^*$ values, as shown in equation (1):

$$\Delta E^* = [(\Delta L^*)^2 + (\Delta a^*)^2 + (\Delta b^*)^2]^{1/2} \quad (1).$$

A negative $\Delta L^*$ indicates a darker sample relative to a control sample, while a positive $\Delta L^*$ indicates a relatively lighter sample. A negative $\Delta a^*$ indicates a sample which is less red than the reference sample, while a positive $\Delta a^*$ indicates that the sample is relatively more red. A negative $\Delta b^*$ indicates a sample which is less yellow than the reference sample, while a positive $\Delta a^*$ indicates that the sample is relatively more yellow. $\Delta C^*$ is related to $\Delta a^*$ and $\Delta b^*$ by equation (2):

$$\Delta C^* = [(\Delta a^*)^2 + (\Delta b^*)^2]^{1/2} \quad (2).$$

The $\Delta E^*$ gives an overall measure of the weatherability of the anthrapyridone compound. For the purposes of this disclosure, if $\Delta E^*$ is less than about 10 it means that the anthrapyridone compound has good weatherability characteristics. Likewise, for the purposes of this disclosure, a value of $\Delta C^*$ of less than 10 means that the brightness of the color is not significantly reduced. It is clear from the data shown in Table 4 that the molded chips prepared using the polymer composition including the anthrapyridone compound of Example 1 maintained good color and color brightness, even after 300 hours of exposure in the weatherometer. Further, the molded chips prepared using the polymer composition including the anthrapyridone compound of Example 2 showed a $\Delta E^*$ value of less than 10 even after 300 hours of exposure in the weatherometer. Furthermore, the molded chips prepared using the polymer composition including the anthrapyridone compound of Example 2 did not indicate much visual difference even after 100 hours.

TABLE 3

$L^*$, $a^*$, $b^*$, $C^*$ and $H^*$ values of the step-chips comprising the anthrapyridone compounds prepared in Example 1 and Example 2 after being weathered for 0, 100, 200 and 300 hours using ASTM D4459 standards.

| Compound of Example | Hours | L* | a* | B* | C* | H* |
|---|---|---|---|---|---|---|
| 1 | 0 | 44.879 | 69.162 | 21.333 | 72.37 | 17.14 |
|   | 100 | 45.03 | 69.082 | 21.057 | 72.22 | 16.95 |
|   | 200 | 44.968 | 69.069 | 21.291 | 72.27 | 17.13 |
|   | 300 | 45.063 | 68.621 | 21.167 | 71.81 | 17.14 |
| 2 | 0 | 39.931 | 67.335 | −54.513 | 86.63 | 321.00 |
|   | 100 | 39.948 | 65.155 | −51.294 | 82.92 | 321.78 |
|   | 200 | 41.063 | 63.89 | −49.943 | 81.09 | 321.98 |
|   | 300 | 42.145 | 61.553 | −47.758 | 77.90 | 322.19 |

TABLE 4

$\Delta L^*$, $\Delta a^*$, $\Delta b^*$, $\Delta C^*$, $\Delta H^*$ and $\Delta E^*$ values of the step-chips comprising the anthrapyridone compounds prepared in Example 1 and Example 2 after being weathered for 0, 100, 200 and 300 hours using ASTM D4459 standards.

| Compound of Example | Hours | ΔL* | Δa* | Δb* | ΔC* | ΔH* | ΔE* |
|---|---|---|---|---|---|---|---|
| 1 | 100 | 0.151 | −0.08 | −0.277 | −0.157 | −0.241 (darker) | 0.325 |
|   | 200 | 0.088 | −0.093 | −0.043 | −0.101 | −0.013 (darker) | 0.135 |
|   | 300 | 0.183 | −0.541 | −0.166 | −0.566 | 0.001 (lighter) | 0.595 |

TABLE 4-continued

ΔL*, Δa*, Δb*, ΔC*, ΔH* and ΔE* values of the step-chips comprising the
anthrapyridone compounds prepared in Example 1 and Example 2 after being
weathered for 0, 100, 200 and 300 hours using ASTM D4459 standards.

| Compound of Example | Hours | ΔL* | Δa* | Δb* | ΔC* | ΔH* | ΔE* |
|---|---|---|---|---|---|---|---|
| 2 | 100 | 1.017 | −2.18 | 3.218 | −3.712 | 1.154 (lighter) | 4.018 |
|   | 200 | 2.132 | −3.45 | 4.570 | −5.541 | 1.431 (lighter) | 6.107 |
|   | 300 | 3.214 | −5.782 | 6.755 | −8.728 | 1.700 (lighter) | 9.455 |

TABLE 3

ΔL*, Δa*, Δb*, ΔC*, ΔH* and ΔE* values of the step-chips comprising the
anthrapyridone compounds prepared in Example 1 and Example 2 after being
weathered for 0, 100, 200 and 300 hours using different external weathering
standards.

| | Test method | Hours | ΔL* | Δa* | Δb* | ΔC* | ΔH* | ΔE* |
|---|---|---|---|---|---|---|---|---|
| Compound of Example 1 | ISO 4892-2A | 100 | 0.118 | −0.031 | 0.064 | −0.01 | 0.07 (lighter) | 0.138 |
| | | 200 | 0.030 | −0.289 | 0.431 | −0.148 | 0.498 (lighter) | 0.52 |
| | | 300 | 0.175 | −0.523 | 0.384 | −0.385 | 0.522 (lighter) | 0.672 |
| | SAE J1960 | 100 | 0.009 | −0.143 | 0.566 | 0.031 | 0.583 (lighter) | 0.583 |
| | | 200 | 0.049 | 0.144 | 1.116 | 0.196 | 1.108 (lighter) | 1.126 |
| | | 300 | 0.082 | −0.344 | 1.287 | 0.059 | 1.331 (lighter) | 1.335 |

While typical embodiments have been set forth for the purpose of illustration, the foregoing descriptions should not be deemed to be a limitation on the scope herein. Accordingly, various modifications, adaptations, and alternatives may occur to one skilled in the art without departing from the spirit and scope herein.

The invention claimed is:

1. An anthrapyridone compound of Formula (I):

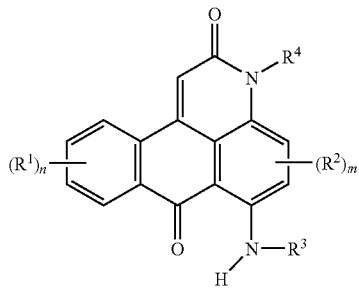

(I)

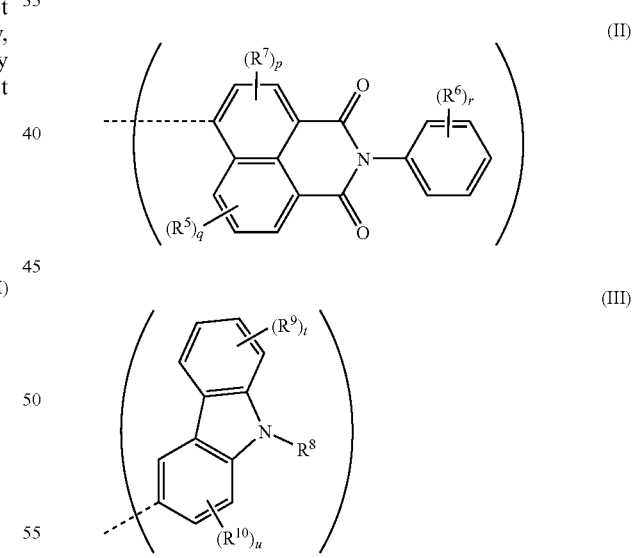

wherein $R^1$ and $R^2$ are independently selected from the group consisting of an aliphatic functionality having 1 to 6 carbon atoms, an aromatic functionality having 3 to 20 carbon atoms, a cycloaliphatic functionality having 3 to 20 carbon atoms, a hydroxy group, a halogen group, and a cyano group; $R^4$ is an aliphatic functionality having 1 to 6 carbon atoms; "n" has a value of 0 to 4; "m" has a value of 0 to 2; and $R^3$ is an aromatic functionality selected from the group consisting of Formula II and Formula III:

wherein $R^5$, $R^6$, $R^7$, $R^9$ and $R^{10}$ are independently selected from the group consisting of an aliphatic functionality having 1 to 6 carbon atoms, an aromatic functionality having 3 to 20 carbon atoms, a cycloaliphatic functionality having 3 to 20 carbon atoms, a hydroxy group, a halogen group, and a cyano group; $R^8$ is an aliphatic functionality having 1 to 6 carbon atoms; "p" has a value of 0 to 2; "q" and "u" each have a value of 0 to 3; "t" has a value of 0 to 4; and "r" has a value of 0 to 5;

further wherein the anthrapyridone compound has a decomposition onset temperature of greater than or equal to 350° C.

2. The anthrapyridone compound of claim 1, wherein $R^1$ and $R^2$ are independently selected from the group consisting of a halogen group, a cyano group, an aliphatic functionality having 1 to 4 carbon atoms, an aromatic functionality having 6 to 12 carbon atoms, and a cycloaliphatic functionality having 6 to 10 carbon atoms.

3. The anthrapyridone compound of claim 1, wherein $R^5$, $R^6$, $R^7$, $R^9$ and $R^{10}$ are independently selected from the group consisting of an aliphatic functionality having 1 to 4 carbon atoms, an aromatic functionality having 6 to 12 carbon atoms, a cycloaliphatic functionality having 6 to 10 carbon atoms, a hydroxy, a halogen group, and a cyano group; $R^8$ is an aliphatic functionality having 1 to 4 carbon atoms; "p" has a value of 0 to 2; "q" and "u" each have a value of 0 to 3; "t" has a value of 0 to 4; and "r" has a value of 0 to 5.

4. The anthrapyridone compound of claim 1, wherein $R^4$ is a methyl group; "n" and "m" each have a value of 0; and $R^3$ is an aromatic functionality having a Formula (IV):

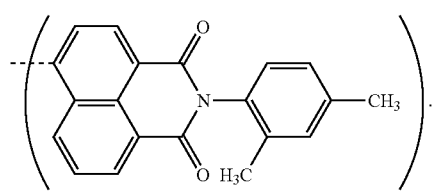

(IV)

5. The anthrapyridone compound of claim 1, wherein $R^4$ is a methyl group; "n" and "m" each have a value of 0; and $R^3$ is an aromatic functionality having a Formula (V):

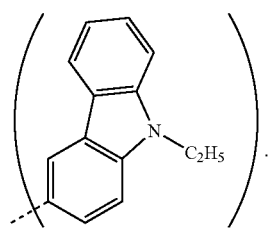

(V)

6. An article comprising the anthrapyridone compound of claim 1.

7. The article of claim 6, comprising the anthrapyridone compound of claim 1 wherein the anthrapyridone compound has a decomposition onset temperature greater than or equal to 350° C.

8. The article of claim 6, wherein the article comprises polycarbonate and from about 0.01 weight percent to about 5 weight percent of the anthrapyridone compound of claim 1 based on the weight of the polycarbonate, wherein the article has a ΔE* of less than 10 after 300 hours when the article is subjected to a weatherability test in accordance with ASTM D4459 test method.

9. The article of claim 6, wherein the article comprises polycarbonate and from about 0.01 weight percent to about 5 weight percent of the anthrapyridone compound of claim 1 based on the weight of the polycarbonate, wherein the article has a ΔC* of less than 10 after 300 hours when the article is subjected to a weatherability test in accordance with ASTM D4459 test method.

10. An anthrapyridone compound of Formula (VI):

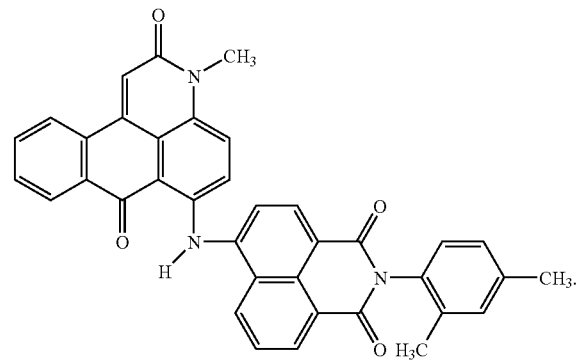

(VI)

11. An anthrapyridone compound of Formula (VII):

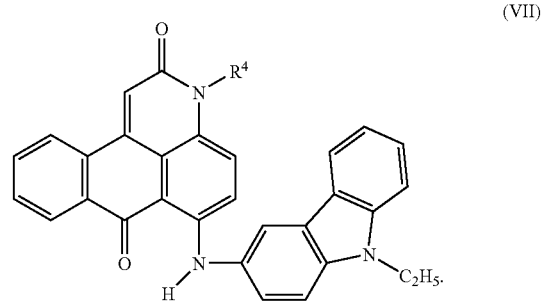

(VII)

12. An article comprising the anthrapyridone compound of claim 10.

13. The article of claim 12, comprising the anthrapyridone compound of claim 10 wherein the anthrapyridone compound has a decomposition onset temperature greater than or equal to 350° C.

14. The article of claim 12, wherein the article comprises polycarbonate and from about 0.01 weight percent to about 5 weight percent of the anthrapyridone compound of claim 10 based on the weight of the polycarbonate, wherein the article has a ΔE* of less than 10 after 300 hours when the article is subjected to a weatherability test in accordance with ASTM D4459 test method.

15. The article of claim 12, wherein the article comprises polycarbonate and from about 0.01 weight percent to about 5 weight percent of the anthrapyridone compound of claim 10 based on the weight of the polycarbonate, wherein the article has a ΔC* of less than 10 after 300 hours when the article is subjected to a weatherability test in accordance with ASTM D4459 test method.

16. An article comprising the anthrapyridone compound of claim 11.

17. The article of claim 16, comprising the anthrapyridone compound of claim 11 wherein the anthrapyridone compound has a decomposition onset temperature greater than or equal to 350° C.

18. The article of claim 16, wherein the article comprises polycarbonate and from about 0.01 weight percent to about 5 weight percent of the anthrapyridone compound of claim 11 based on the weight of the polycarbonate, wherein the article has a ΔE* of less than 10 after 300 hours when the article is subjected to a weatherability test in accordance with ASTM D4459 test method.

19. The article of claim 16, wherein the article comprises polycarbonate and from about 0.01 weight percent to about 5 weight percent of the anthrapyridone compound of claim 11 based on the weight of the polycarbonate, wherein the article has a ΔC* of less than 10 after 300 hours when the article is subjected to a weatherability test in accordance with ASTM D4459 test method.

* * * * *